US008574276B2

(12) United States Patent
Gourgouliatos et al.

(10) Patent No.: US 8,574,276 B2
(45) Date of Patent: *Nov. 5, 2013

(54) FIBER OPTIC BRUSH FOR LIGHT DELIVERY

(75) Inventors: Zafirios Gourgouliatos, Los Angeles, CA (US); David Chang, Encino, CA (US)

(73) Assignee: Lerner Medical Devices, Inc., Los Angeles, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/014,482

(22) Filed: Jan. 15, 2008

(65) Prior Publication Data

US 2008/0172115 A1 Jul. 17, 2008

Related U.S. Application Data

(60) Provisional application No. 60/880,887, filed on Jan. 17, 2007, provisional application No. 60/880,813, filed on Jan. 17, 2007, provisional application No. 60/880,883, filed on Jan. 17, 2007, provisional application No. 60/880,812, filed on Jan. 17, 2007.

(51) Int. Cl.
*A61N 5/06* (2006.01)

(52) U.S. Cl.
USPC .................................. 607/88; 607/94; 607/89

(58) Field of Classification Search
USPC .................. 607/94, 1, 88; 606/9, 16
See application file for complete search history.

(56) References Cited

U.S. PATENT DOCUMENTS

| 2,397,757 | A | * | 4/1946 | Schwedersky | 607/79 |
| 3,261,978 | A | * | 7/1966 | Brenman | 15/105 |
| 3,590,232 | A | * | 6/1971 | Sadowski | 362/573 |
| 4,423,531 | A | | 1/1984 | Wall | |
| 4,520,816 | A | | 6/1985 | Schacher et al. | |
| 4,558,700 | A | | 12/1985 | Mutzhas | |
| 4,653,495 | A | * | 3/1987 | Nanaumi | 606/16 |
| 4,898,439 | A | * | 2/1990 | Mori | 385/31 |
| 5,300,097 | A | * | 4/1994 | Lerner et al. | 607/93 |
| 5,402,768 | A | * | 4/1995 | Adair | 600/106 |
| 6,053,180 | A | * | 4/2000 | Kwan | 132/232 |
| 6,074,411 | A | | 6/2000 | Lai et al. | |
| 6,254,625 | B1 | | 7/2001 | Rosenthal et al. | |
| 6,270,492 | B1 | | 8/2001 | Sinofsky | |

(Continued)

OTHER PUBLICATIONS

Taneja, A. et al., "Broad-band UVB fiber-optic comb for the treatment of scalp psoriasis: a pilot study", *International Journal of Dermatology*, vol. 43, pp. 462-467, 2004.

(Continued)

*Primary Examiner* — Bill Thomson
*Assistant Examiner* — Jeffrey Lipitz
(74) *Attorney, Agent, or Firm* — Lathrop & Gage LLP

(57) ABSTRACT

A phototherapy apparatus is disclosed including: a body member; a plurality of elongated light transmitting elements, each of the elements extending between a proximal end enclosed within the body member and a distal end located outside of and distal to the body member; where the tips of the proximal ends of the light transmitting elements are located in close proximity to each other; and an optical connector configured to detachably receive an end of a lightguide and to couple light delivered by the lightguide from a source into the light transmitting elements at the proximal ends. The light coupled into each of the light transmitting elements is transmitted along the element and emitted from the distal end.

40 Claims, 13 Drawing Sheets

(56) References Cited

U.S. PATENT DOCUMENTS

| | | | |
|---|---|---|---|
| 6,447,537 | B1 | 9/2002 | Hartman |
| 6,494,899 | B1 | 12/2002 | Griffin et al. |
| 7,194,316 | B2 * | 3/2007 | Bousfield et al. ............. 607/150 |
| 2001/0025190 | A1 * | 9/2001 | Weber et al. .................... 607/89 |
| 2002/0038485 | A1 | 4/2002 | Nakagawa et al. ................ 15/28 |
| 2002/0128696 | A1 * | 9/2002 | Pearl et al. ...................... 607/89 |
| 2002/0133144 | A1 | 9/2002 | Chan et al. |
| 2002/0156402 | A1 * | 10/2002 | Woog et al. ..................... 601/46 |
| 2003/0057385 | A1 | 3/2003 | Magne et al. |
| 2003/0076281 | A1 | 4/2003 | Morgan et al. |
| 2003/0233138 | A1 | 12/2003 | Spooner |
| 2005/0135102 | A1 | 6/2005 | Gardiner et al. |
| 2005/0143793 | A1 | 6/2005 | Korman et al. |
| 2005/0154382 | A1 | 7/2005 | Altshuler et al. |
| 2005/0251242 | A1 * | 11/2005 | Bousfield et al. ............. 607/150 |
| 2005/0267452 | A1 | 12/2005 | Farr et al. |
| 2006/0178712 | A1 * | 8/2006 | Carullo et al. .................. 607/89 |
| 2006/0200115 | A1 | 9/2006 | Ferren et al. |
| 2006/0276862 | A1 | 12/2006 | Irwin |
| 2007/0060984 | A1 * | 3/2007 | Webb et al. ..................... 607/89 |
| 2007/0179574 | A1 * | 8/2007 | Elliott ............................. 607/94 |

OTHER PUBLICATIONS

PCT International Search Report (PCT/US08/00495); Date of mailing Jun. 18, 2008; 1 page.

PCT International Search Report (PCT/US08/00499); Date of mailing Jul. 7, 2008; 1 page.

PCT International Search Report (PCT/US08/00545); Date of mailing Jul. 11, 2008; 1 page.

* cited by examiner

| Type | Typical UVB MED of unexposed skin (mJ/cm$^2$) | Recommended Start Dose @ 2 MEDs (mJ/cm$^2$) | Recommended End Dose* (mJ/cm$^2$) |
|---|---|---|---|
| I | 45 | 90 | 240-360 |
| II | 75 | 150 | 600-750 |
| III | 90 | 180 | 720-950 |
| IV | 120 | 240 | 900-1,100 |
| V | 150 | 300 | 1,000-1,200 |
| VI | 240 | 480 | 1,200-1,400 |

*Depending on patient tolerance.

Treatment doses for Wavelength Optimized UV-B.

Fig. 9

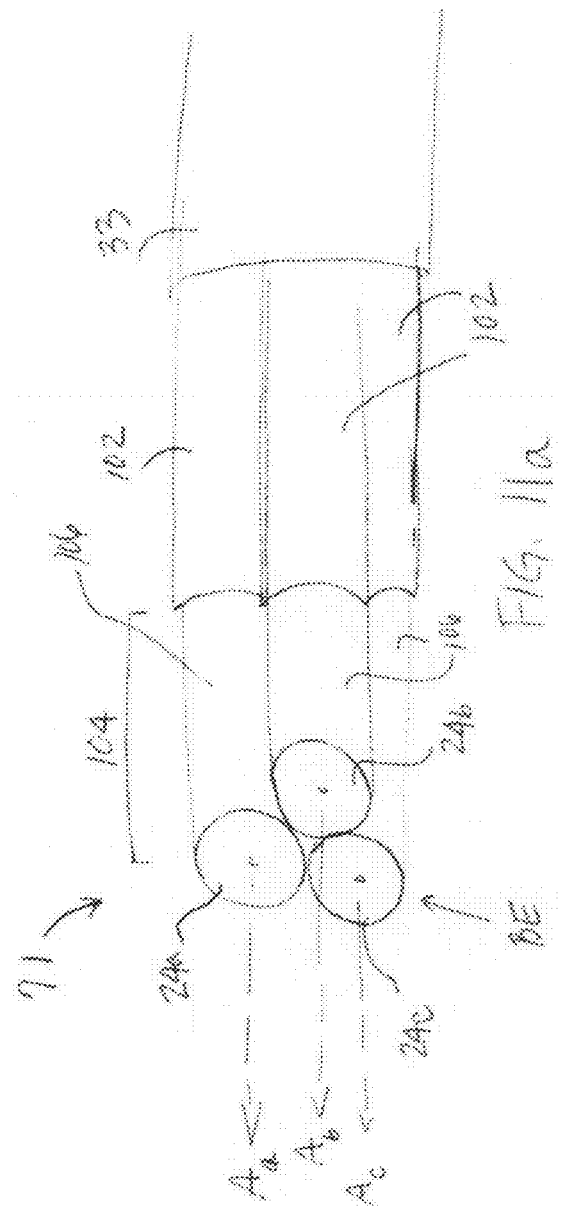
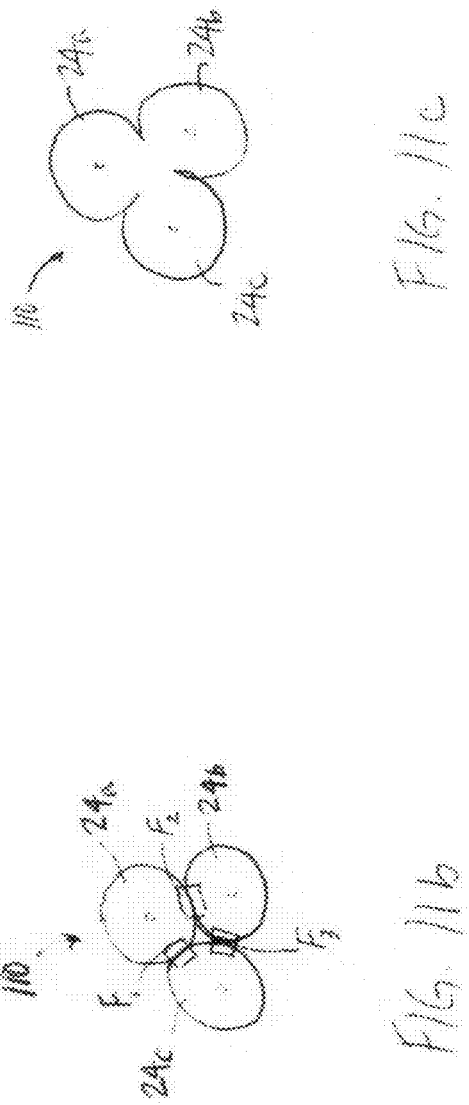

FIBER OPTIC BRUSH FOR LIGHT DELIVERY

CROSS REFERENCE TO RELATED APPLICATIONS

The present application claims priority from U.S. Provisional Application Ser. No. 60/880,883, U.S. Provisional Application Ser. No. 60/880,812, U.S. Provisional Application Ser. No. 60/880,813, U.S. Provisional Application Ser. No. 60/880,887, each filed Jan. 17, 2007, and each of which is incorporated by reference herein in its entirety.

BACKGROUND

This disclosure relates to phototherapy treatments for inflammatory diseases of the skin located on the scalp and other parts of the body covered by hair and more specifically to treatment of ultraviolet light-responding dermatoses.

Inflammatory diseases of the skin affect a large portion of the population resulting in significant morbidity. Psoriasis, for example, affects at least 1% of the population. This disease involves an abnormally fast rate of cell proliferation in the basal layer of the epidermis giving rise to red, scaly plaques and bleeding when traumatized (the "Auspitz sign"). Past methods of treatment of skin psoriasis include the application of tars, salicylic acid, steroids, ultraviolet light (phototherapy), and a combination of ultraviolet light, used in conjunction with photoactive compounds (photochemotherapy).

Photochemotherapy involves treatment with ultraviolet radiation of an affected area in combination with a topically or systemically applied medicament that sensitizes the skin to ultraviolet radiation (e.g., psoralen). Typically ultraviolet-A (UV-A) light (so-called long wave UV light) having wavelengths from 310 to 440 nm is used for this purpose. Unfortunately, successful treatment requires that UV radiation must be applied until an erythema (sunburn) is created. In some cases, the eyes of patients systemic undergoing psoralen and topical UV treatment may be sensitized to sunlight for several hours after treatment. In addition, some patients find the medicament difficult to tolerate. Furthermore, this therapy requires 20-25 radiation sessions which result in darkening of the pigmentation of the skin. In addition, treatment of scalp psoriasis in particular has been limited by two other problems. First, patients are reluctant to apply medications regularly which must remain on their scalps for hours at a time. Second, light from conventional treatment devices does not effectively penetrate hair covering the scalp.

Phototherapy involves simply UV irradiation of the affected area. For example, psoriasis has been treated with ultraviolet-B (UV-B) light having wavelengths from 290-320 nm. Other skin diseases which have been treated successfully with ultraviolet light include eczema, mycosis fungoides, and lichen planus. In addition, ultraviolet light may have a role in the treatment of seborrheic dermatitis.

Phototherapeutic methods have included the use of mercury vapor high pressure radiation devices and those UV sources having varying spectral distribution. For example, UV-B lamps such as devices which produce radiation from a metal halide or mercury vapor source and which filters the emitted UV light with colored glass have been used (see e.g., U.S. Pat. No. 4,558,700). These devices emit UV in the range of 270-365 nm (mostly 270-315 nm), and cause erythema. Devices which emit wavelengths of 320-330 nm and greater have also been used for so-called super-high-intensive phototherapy (SHIP).

A prior art device is adapted to deliver UV radiation to the scalp. That device is a hair brush for purportedly promoting the healthy flow of blood to the glands and roots of hair, and for promoting vitamin D production. The hair brush has an internal UV radiation source and UV radiation-transmitting bristles of a material other than a fiber optic material (Schwedersky, U.S. Pat. No. 2,397,757). Because the bristles of this device are rigid and pointed, its use on psoriasis-affected skin heightens the incidence of the Auspitz sign, and thus is contra-indicated for treatment of psoriasis.

Lerner et al., U.S. Pat. No. 5,300,097 describes a light delivery apparatus which includes a body member and a plurality of optical fibers extending therefrom. The optical fibers are adapted to couple the light generated at the optical source from the proximal tips of the optical fibers, through the fibers, and to their distal tips. Each fiber has a proximal tip affixed to the body member and a distal tip at the end opposite the proximal tip. Also described are methods of treating inflammatory dermatoses using the light delivery apparatus. The method includes contacting a region of the body afflicted with a dermatosis with the distal tips of the device such that UV light emanating therefrom is incident on the contacted region. In some cases, the method includes the additional step of, prior to the contacting step, applying a medicant or lubricant to the region to be treated.

Therefore, a need exists for a simple device and method useful for treating affected areas of the skin, particularly those hair-covered regions such as the scalp.

SUMMARY

The present disclosure describes a phototherapy delivery device for effective treatment of inflammatory dermatoses such as psoriasis in hair bearing areas of the skin such as the scalp and scrotum. This device comprises of a fiberoptic based light delivery apparatus.

In light of the above, it is an object of this disclosure to provide a therapeutic device for the delivery of UV irradiation directly to an area of the body afflicted with psoriasis or other related dermatoses.

Yet another object is to provide a method of treating psoriasis and related dermatoses which is easy to administer, rapid, and which minimizes unpleasant side effects such as erythema, pigmentation darkening, and the Auspitz sign.

An additional object of the disclosure is to provide a method of treating psoriasis which minimizes the therapeutic sessions required to result in relatively rapid healing.

In one aspect, a phototherapy apparatus is disclosed including: a body member; a plurality of elongated light transmitting elements, each of the elements extending between a proximal end enclosed within the body member and a distal end located outside of and distal to the body member; where the tips of the proximal ends of the light transmitting elements are located in close proximity to each other; and an optical connector configured to detachably receive an end of a lightguide and to couple light delivered by the lightguide from a source into the light transmitting elements at the proximal ends. The light coupled into each of the light transmitting elements is transmitted along the element and emitted from the distal end.

In some embodiments, the light transmitting elements each include an optical fiber.

In some embodiments, the light transmitting elements are detachably affixed to the body member. Some such embodiments include a support plate adapted to be detachably received by the body member and to support the elongated light transmitting elements. Each of the elongated light transmitting elements extend through the support element from a side of the support element proximal the body member to a side of the support element distal the body member. In some embodiments, the support plate is affixed to the body member with an adhesive.

In some embodiments, the proximal ends of the light transmitting elements include a fiber bundle, the bundle having an entrance face included of the tips of the proximal ends.

In some embodiments, the fibers of the fiber bundle are fused together in proximity to the entrance face. Some embodiment include an optically transparent window positioned in proximity to the entrance face. In some embodiments, each of the fibers in the fiber bundle include an inner core surrounded by a cladding, and where the cladding is stripped away from a portion of the fiber in proximity to the entrance face. In some embodiments, the fiber bundle includes an optically clear material filling interstitial spaces between the fibers in the bundle in proximity to the entrance face. Some embodiments include a ring adapted to secure the fibers in the fiber bundle in close proximity to each other.

In some embodiments, the optical connector is adapted to hold an end of the lightguide in fixed spatial alignment with the face of the fiber bundle.

In some embodiments, the distal ends of the light transmitting elements are arranged in an array. In some embodiments, the array is a two dimensional array. In some embodiments, the tips of the distal ends of the light transmitting elements are located at positions in space having a locus characterized by a curved surface or arc. In some embodiments, the curved surface or arc includes one of the group of: a circular arc, a parabolic arc, and ellipsoidal arc, a cylindrical segment, a spherical segment, a toroidal segment. In some embodiments, the curved surface or arc has an associated radius or radii or curvature within the range of about 2 inched to about 6 inches. In some embodiments, the locus is adapted to substantially conform to the shape of a human scalp In some embodiments, the array is arranged to provide substantially uniform fluence of light emitted from the distal ends of the light transmission elements at an area of a treatment surface.

In some embodiments, the distal end of one or more of the light transmitting elements includes a bulbous tip included of a light emitting spherical segment. The spherical segment may have a radius of curvature within the range of about 0.25 mm to about 3.0 mm In some embodiments, the distal end of one or more of the light transmitting elements includes a rounded tip. The rounded tip may have a radius of curvature within the range of about 0.25 mm to about 3.0 mm In some embodiments, one or more of the optical fibers includes an inner core surrounded by an outer cladding, the inner core having a radius within the range of about 0.1 mm to about 3 mm.

In some embodiments, the elongated light transmitting elements are autoclavable.

Some embodiments include a cap adapted for removable connection to the body member, the cap adapted to, when connected to the body member, enclose the distal ends of the light transmitting elements. In some embodiments, the cap includes an optical diffuser element disposed between the tips of the distal ends of the light transmitting elements and a treatment area.

Some embodiments include a control unit enclosed in the body member where the control unit is in communication with the light source, and the control unit adapted to selectively adjust the duration or intensity of light provided from the source through the lightguide.

Some embodiments include a sensor adapted to determine information indicative of the intensity of light emitted from the distal ends of the light transmitting elements. In some embodiments, the control unit is configured to, based on the information indicative of the intensity of light o from the distal ends of the light transmitting elements, adjust the duration or intensity of light provided from the source to maintain constant output intensity. Some embodiments include a dosimetry sensor adapted to, during operation, provide to the control unit information indicative of a dose of treatment light directed from the light transmitting elements to a treatment surface. In some embodiments, the control unit is configured to selectively adjust the duration and intensity of light coupled into the light transmitting elements based on the information indicative of the dose of treatment light.

In some embodiments, the body element is substantially opaque to ultraviolet light.

Some embodiments include the lightguide and the source. In some embodiments, the source has a spectral range within the range of 280 nm to 320 nm, within the range of 308 nm to 320 nm, within the range of 320 nm to 380 nm. In some embodiments the source includes at least one of the group of: a lamp, a laser, an excimer laser, a diode laser, a light emitting diode, an excimer gas discharge lamp.

Some embodiments include a sensor adapted to sense the proximity or contact of the distal end of one or more of the elongated light transmitting elements to a treatment surface, the sensor being in communication with the control unit.

Some embodiments include an auditory signal transducer in communication with the control unit.

In some embodiments, one or more of the light transmitting elements includes a substance adapted to change color in a fashion indicative of the state of use of the fiber.

In some embodiments, one or more of the elongated light transmitting elements includes a hollow tube, the interior surface of the tube having a reflective coating.

In another aspect, a method of treating an area of skin affected by skin disease is disclosed including providing an effective dose of treatment light to the affected area with a phototherapy device. The device includes: a body member; a plurality of elongated light transmitting elements, each of the elements extending between a proximal end enclosed within the body member and a distal end located outside of and distal to the body member. The tips of the proximal ends of the light transmitting elements are located in close proximity to each other. The device also includes an optical connector configured to detachably receive an end of a lightguide and to couple light delivered by the lightguide from a source into the light transmitting elements at the proximal ends. The light coupled into each of the light transmitting elements is transmitted along the element and emitted from the distal end. In some embodiments, the treatment light includes ultraviolet light.

In some embodiments, providing treatment light includes bringing the distal ends of the light transmitting elements into proximity or contact with the affected area.

In some embodiments, providing treatment light includes, while maintaining distal ends of the light transmitting elements into proximity or contact with the affected area, moving the distal ends across the affected area to provide at least one minimal erythema dose of treatment light to substantially the entire the affected area.

In some embodiments, at least a portion of the affected area is a hair bearing region, and moving the distal ends across the affected area includes combing the distal ends through the hair.

It is to be understood that, as used herein, skin disease includes inflammatory skin disease such as psoriasis, vitiligo, pigmentation loss, and other disorders.

Various embodiments may include any of the above described features, alone or in any combination. These and other features will be more fully appreciated with reference to the following detailed description which is to be read in conjunction with the attached drawings.

DESCRIPTION OF THE DRAWINGS

The foregoing and other objects of this disclosure, the various features thereof, may be more fully understood from the following description, when read together with the accompanying drawings in which:

FIG. 9 is an exemplary phototherapy dosage table;

FIG. 11a is a perspective view showing the bundle end of a group of fibers of the present invention;

FIG. 11b is an end cross-section view of the fiber bundle of FIG. 11a;

FIG. 11c is an end cross-section view of a fused fiber bundle of the present invention;

Like reference numerals refer to like elements throughout the figures.

DESCRIPTION

Figure 1A:
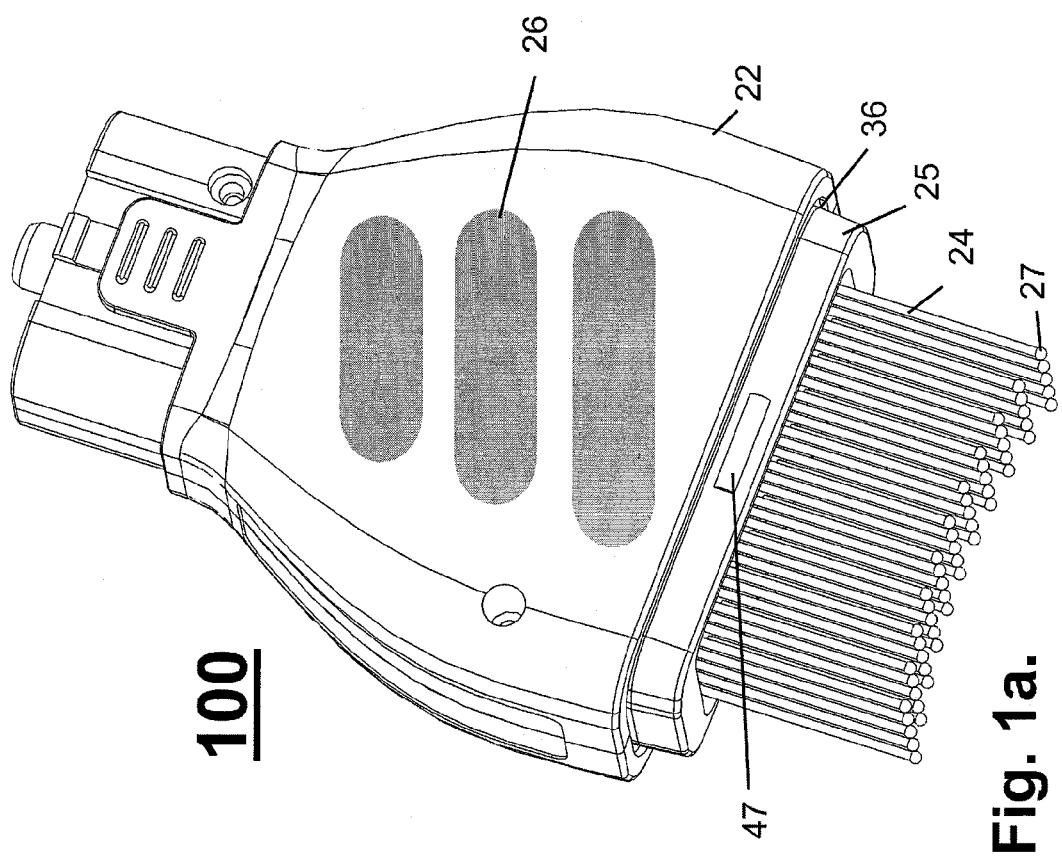
FIG. 1a is a perspective view showing an exemplary fiberoptic light delivery device.
Figure 1B:
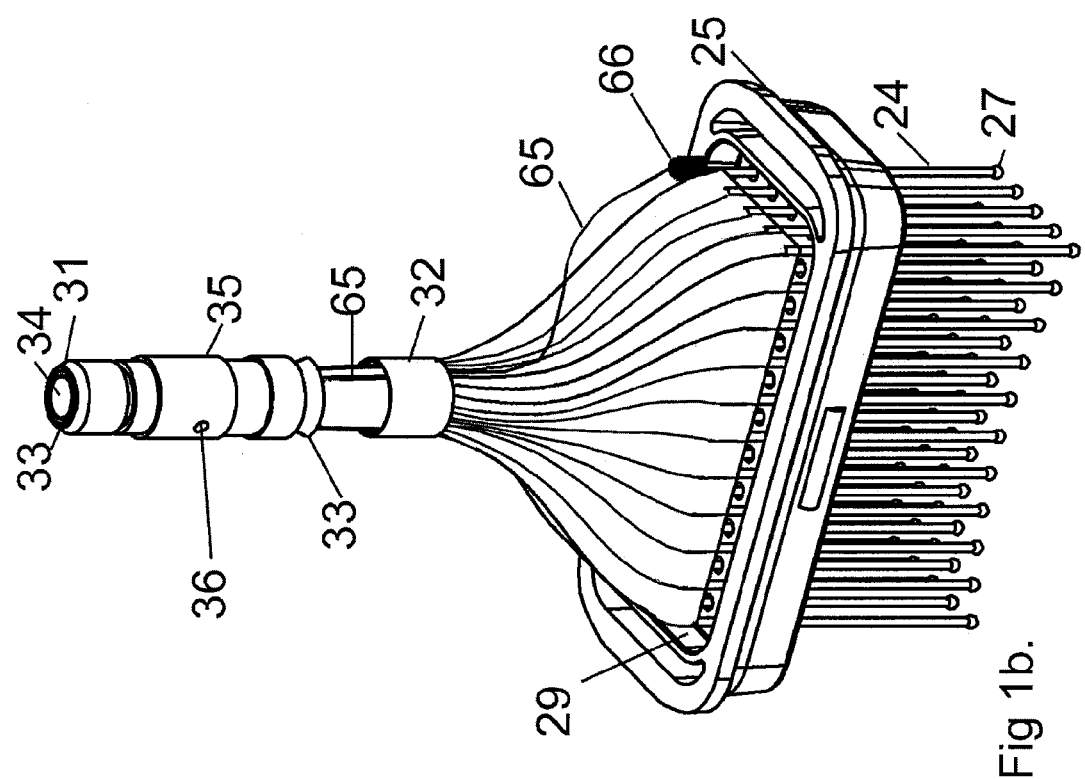
FIG. 1b is a perspective view showing an exemplary fiberoptic light delivery device with shell removed.
Figure 4B:
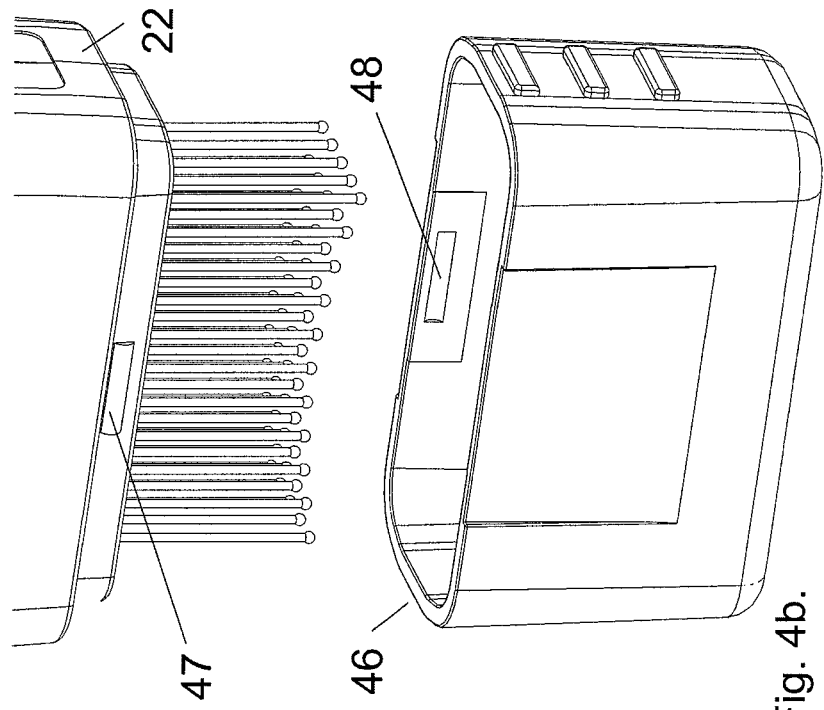
FIG. 4b shows the same detached.
Figure 4A:
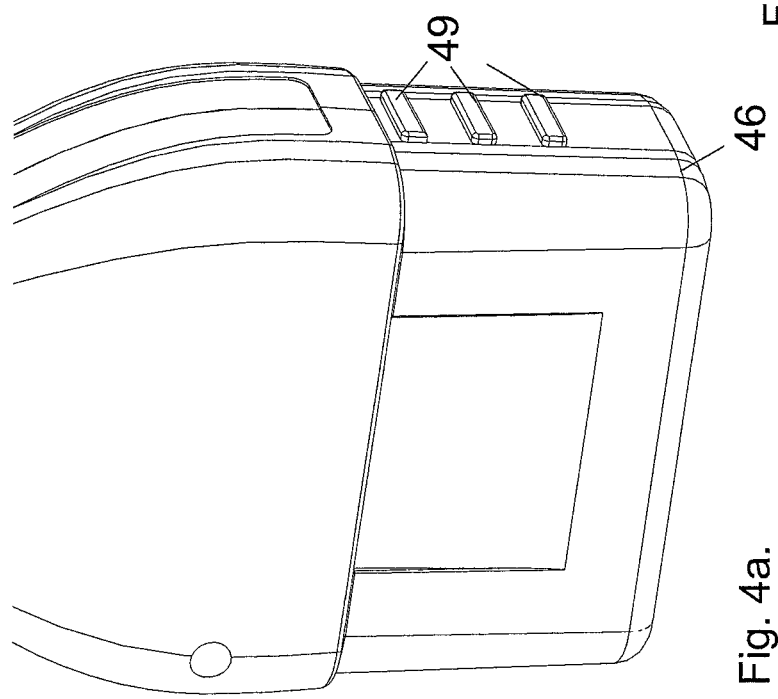
FIG. 4a shows the protection and rinse cap attached to the device.
Figure 5B:
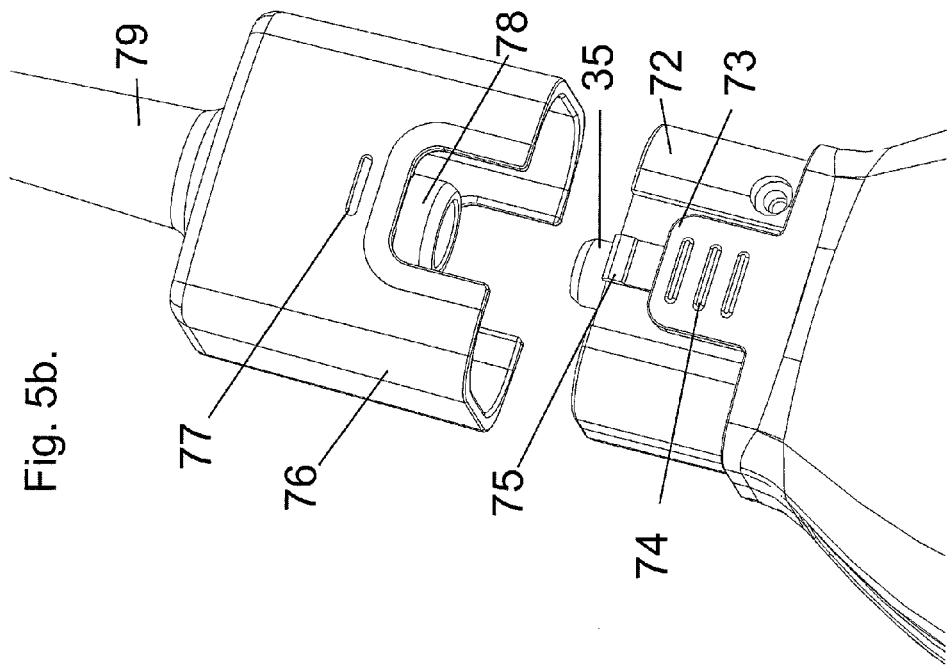
FIG. 5a show the connector configuration at the input side and FIG. 5b shows the same connector detached
Figure 5A:
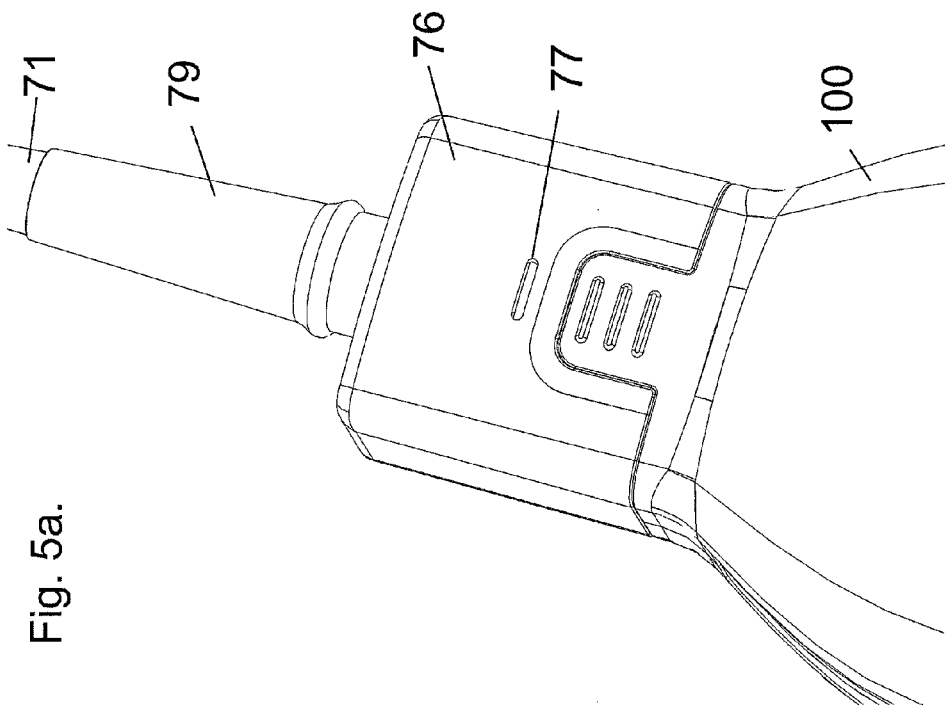

Therapeutic device 100 is shown in FIG. 1a, and includes a light delivery apparatus including body member 22 and a plurality of light transporting elements, such as optical fibers 24 extending therefrom. The light transporting elements are affixed on a support plate 25. Body member 22 encloses the remainder of the light transporting elements (shown in FIG. 1b). The lower end of the body can form a receptacle for a detachable cap 46 (shown in FIGS. 4a and b). The cap can be a rinse cap or cap with diffusers attached. The body 22 can have alternative configurations so that it embodies of provides for the attachment of handles for more security and comfort of handling during use.

Preferably, body member 22 has substantially no UV-transferring abilities, and is formed of a molded resinous material, such as plastic, rubber, and the like. Preferably, body member preferably has ribs or knurls 26 for more secure holding by the operator.

Figure 2:
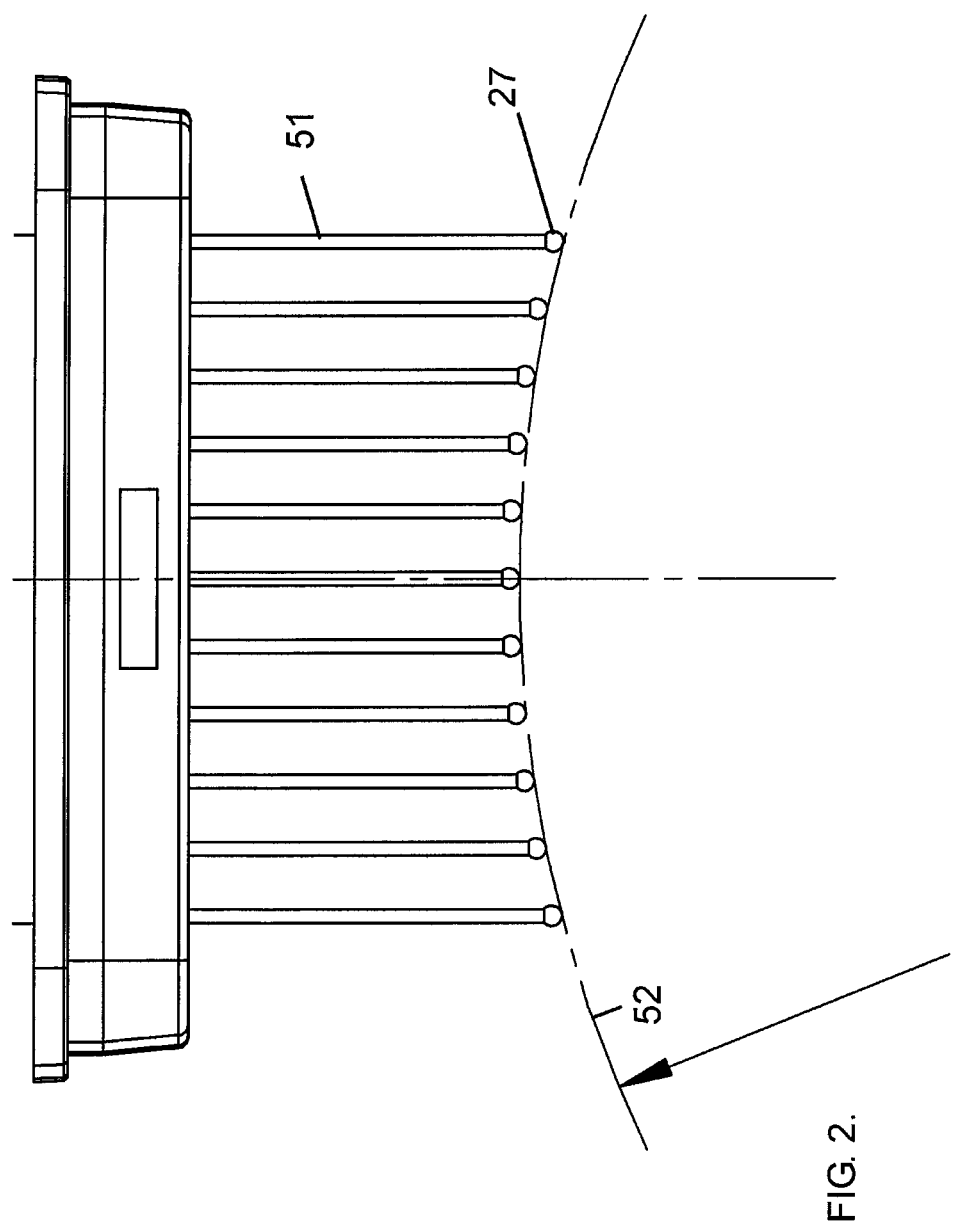
FIG. 2 shows a detail of a fiber tip arrangement.

The light transporting elements can be distally arranged in a grid or rows and columns. In FIG. 1a an embodiment of 5 rows and 11 columns is shown. The light transporting elements can also be arranged in a single line 51 as shown in. FIG. 2. The length of the light transporting elements is reasonable for combing action while maintaining skin contact and is typically in the range of 0.5 to 2.5 inches. The distance between each of the light transporting elements is in the range of 0.05 to 0.5 inches. The grid depicted is square but it can also be a slanted rectangular, zigzag, honeycomb or semi random for better spreading of light delivery when combing. The size of outline of the grid is preferable in the range of 0.5 to 2 inches in width and 0.5 to 5 inches in length. When the fiber arrangement is in single line, the length of the profile can be between 0.5 and 15 inches. The larger sized profile, combined with a curved arrangement of the tips of the fibers will potentially deliver light on the scalp in a single pass. An array of these lines can be also made in the form of dome shaped, helmet like hair-dryer to treat the whole scalp at once.

The light transporting elements can be single optical fibers with diameter 400 um to 2 mm (preferably 600 um for array, 800 um for in line) or fiber bundles. Central core is composed of a material which is capable of transmitting Visible and/or UV irradiation, such as fused silica, solarization resistant fused silica, plastic, or glass. The cladding can be a lower refractive index polymer cladding (giving a 0.2 to 0.51 NA, typically 0.39 NA). The outer jacket can be Teflon, nylon or formable resinous material, such as plastic, silicone, rubber, and the like. Cladding material can also be a lower refractive index glass or fused silica cladding (0.1 to 0.31 NA, typically 0.22 NA). The later provide the option of being fused together at the receiving end a feature that makes it suitable for Excimer Laser use. Of course, in some alternative embodiment, the light transmitting element can be a hollow or filled tube with internal diameter of 0.1-3 mm with polished, UV reflecting internal surface. The tubes can be cylindrical or conical or a combination of these two surfaces. Fibers 24 are hardy and ideally autoclavable or able to be gas sterilized.

The distal tips 27 of the light transporting elements can be arranged on a straight line if a single row or on a plane if an array. They can also be preferably arranged on a curved line 52 (shown on FIG. 3) or curved surface to match the shape of the scalp. The curved line can potentially resemble an arc of a circle, parabola, ellipsoid or other curved line. If an arc of a circle, the radius of the circle can be in the range of 2 to 6 inches to accommodate different scull sizes. In the case of an array, the surface can be part of a cylinder, sphere, toroidal, ellipsoidal or other curved surface. If a cylindrical surface is chosen, the radius of the cylinder can be in the range of 2 to 6 inches to accommodate different scull sizes. In a similar manner if a spherical or toroidal surface is chosen, the radius or radii can be in the range of 2 to 6 inches.

Distal tips 27 of fibers 24 are spherical segments. In the embodiment of FIG. 1a, those tips have a UV light transmitting spherical element or are just rounded. The distal tips have a radius of curvature in the range of about 0.25-3.0 mm, to ensure that minimal damage is done to the skin during use. They should be smooth and small enough to easily be moved through the hair in brush-like fashion. The Ball tips can be made of epoxy substances, molded plastic, fused silica, sapphire, or other materials that allow light transmission.

The therapeutic light will be coupled from the light source to the fiberoptic brush via a light guide that can be a fiber bundle 71 or a liquid filled flexible tube. For improved coupling the fibers need to be brought together at the receiving end 31 and form a fiberoptic bundle. In order for the fibers to be mechanically held together a ring 32 is preferentially placed where the fibers are brought together. For light loss minimization at the coupling with the light guide the fibers are preferentially brought together tightly and the space in between the core is minimized. For this reason, the fibers 24 are stripped of the cladding 102 at the bundle end BE, as shown in FIG. 11a. To allow for stress distribution as the fibers are bent from the jacket covered portion to the tip, the stripped portion 104 can be in the range of 0.5 to 4 inches. Because for each fiber the length of the portion between the ring 32 and the fiber support plate 25 is variable, the jacketed portion that corresponds to this length is also correspondingly variable so that the end of the jacketed portion is preferentially at the same height from the fiber support plate 25 and at the proximity of the top of the ring 32. The remaining length from the top of the ring to the receiving end 31 is preferentially equal for each fiber.

At the receiving end the fibers are kept together with a tube 33, extending from the receiving end to the proximity of ring 32 with such size as to minimize the space between the fiber cores 106, as shown in FIG. 11a for an exemplary 3-fiber bundle. The tube can be cylindrical, cylindrical with flared edges, conical, or of a manifold shape that reduces the diameter from the bottom to the top and provide for the distribution of stresses as the fibers are brought together, from being apart from each other due to the separation by the jacket that reaches the top of the ring, to the tight fit in the tube. Ideally, the fibers are fused together at points F1, F2, F3 as shown in FIG. 11b, to eliminate the empty space between them, for example, as shown in FIG. 11c. As shown in FIG. 11a, the fibers 24a, 24b, 24c of each fiber bundle 71 extend along an input axes Aa, Ab, Ac.

If the fibers are not fused, the space between the fibers in the tube is filled with an optically clear material. This material provides for mechanical fixation and disallows for empty space between the fibers that can trap contamination. Additionally or alternatively, a transparent window 34 can be placed on the top of the bundle. This window, in addition to protection from contamination, can have optical properties to provide filtering of the light that enters the brush. Preferred materials for this window are quartz, or low-cut-UV-transmissive glasses.

For improved transmission the tips of the fibers can be cut with a method that provides a smooth surface, such as with a diamond wheel or a laser, and then polished.

The fiber support plate 25 has a cavity 29 that can be filled with adhesive for mechanical fixation of the fibers and for improved stability given that the fibers will be subjected to pull-out forces with the brushing action, especially if a hair snarl is encountered.

The fiber support plate 25 and the outer shell 22 can create a groove shaped cavity 36 at the area where they meet to place a sealing material and disallow liquids from entering the interior of the brush through the space between them.

A cap 46 (FIGS. 4a and 4b) can be detachably attached to the Fiberoptic Brush. This cap will protect the fibers during shipping and storage and will also serve as a rinsing container for cleaning the brush. The cap is secured on the brush by a protrusion 47 that fits into the indent 48 of the cap. The cup has ribs 49 or knurls for holding. By compressing the cap at the ribs the fit from the protrusion 47 to the indent 48 is relaxed and the cup is easily removable.

Figure 3:
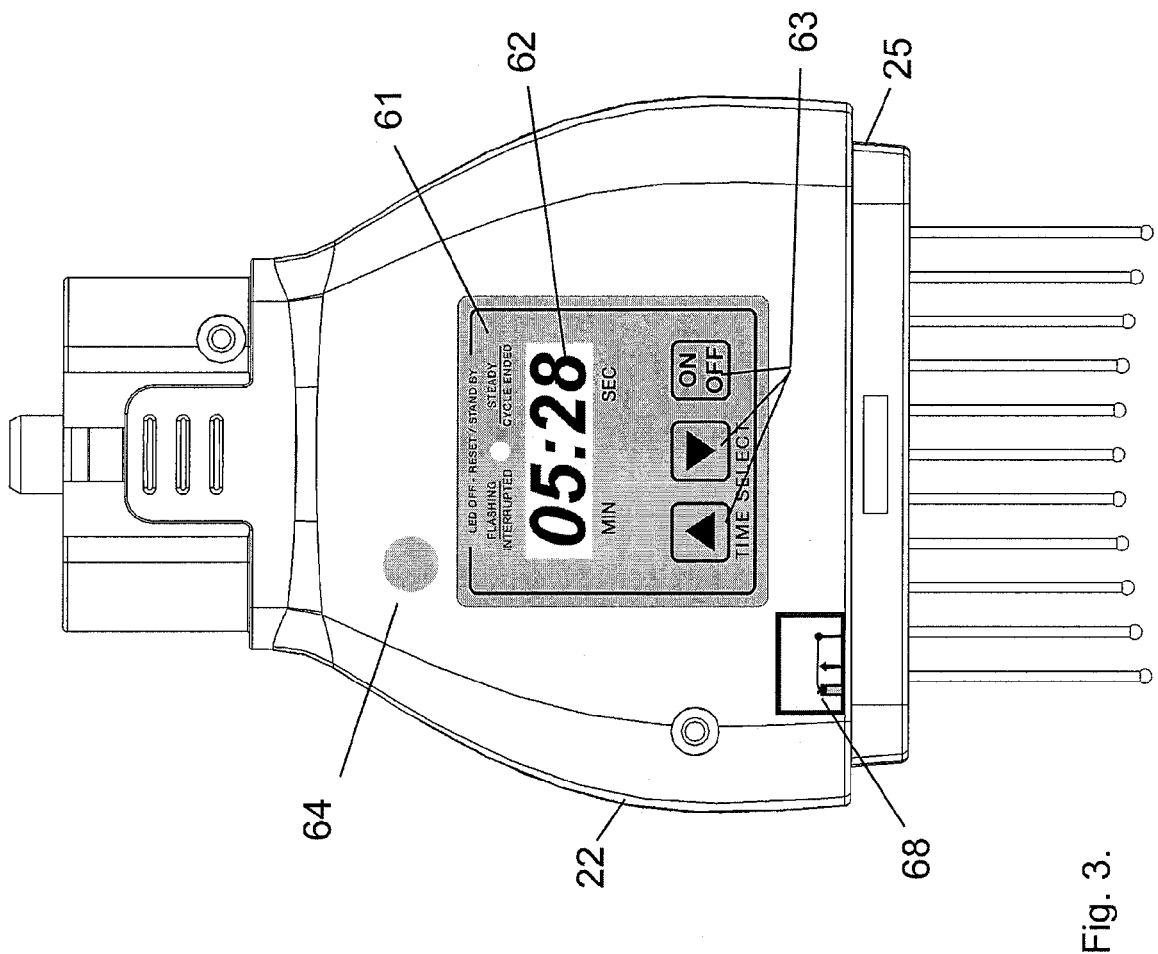
FIG. 3 shows an alternative embodiment of the device of FIG. 1 where a status indicator, control buttons and an auditory signal transducer is included in the assembly.
Figure 12:
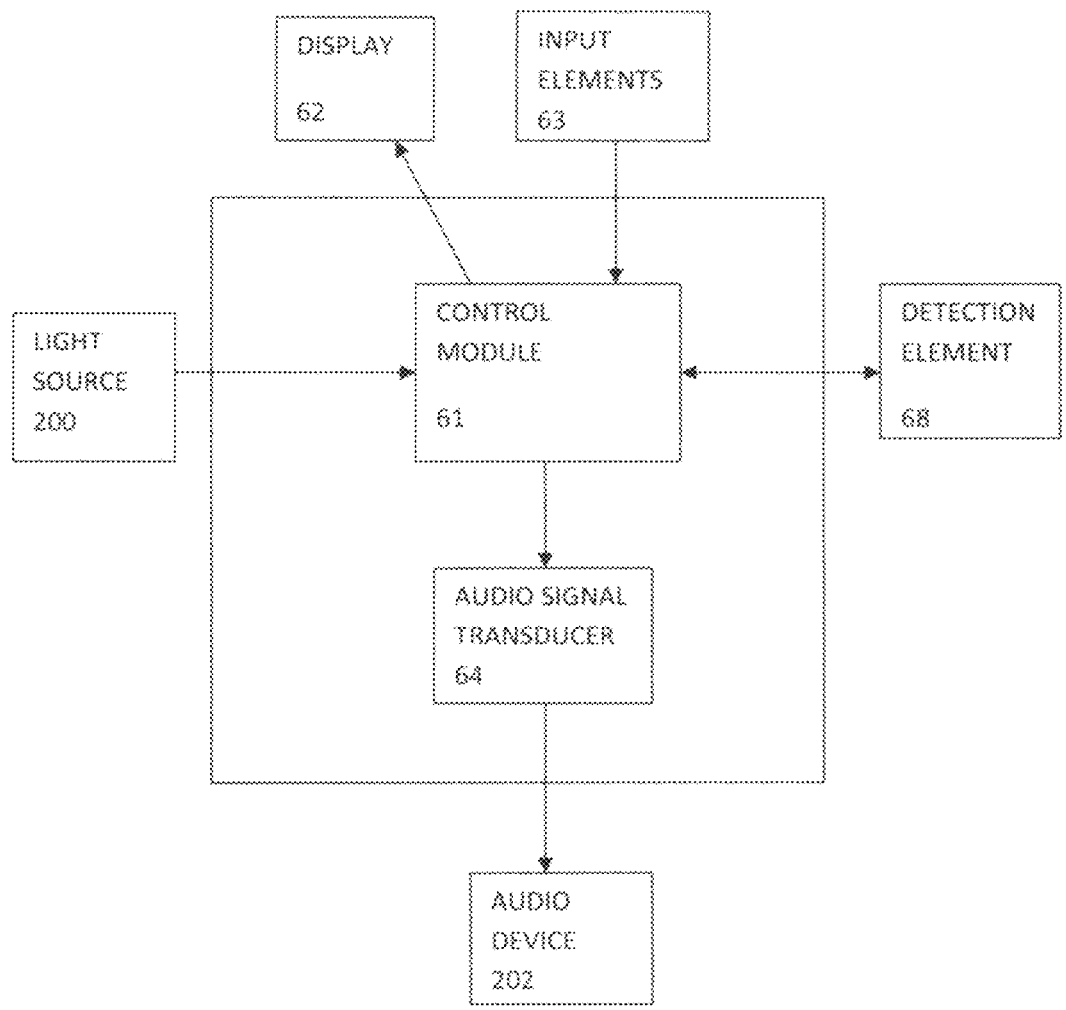
FIG. 12 is a block diagram of a fiberoptic light delivery device of the present invention.

The treatment parameters need to be set before use of this fiberoptic brush. Typically, the controls that set the treatment are located on the light source 200 (see FIG. 12). In the embodiment of FIG. 3 the controls are embodied in the fiberoptic brush for convenience to the user. In summary, and as shown in FIG. 3, as viewed together with FIG. 12: body member 22 can include control module 61 with display 62 and input elements 63 on body member surface, auditory signal transducer 64 for operator warnings via an audio device 202. Communication with the light source 200 that supplies the light can be achieved either by wire, fiber optic connection or with a wireless transmitter and receiver.

A detection element 68 (FIG. 3) on the plate or between the body member 22 and plate 25 detects proximity or contact of fiber distal tips to the epidermis. This detection element communicates with the control module.

The light transporting element bundle can include an additional fiber 65 coupled to a detector 66 that detects the output level and sends a signal to the control element for output detection and stabilization.

The light transporting element bundle can include an additional fiber 93 coupled to a portion of the body member 94 that is made out of material that changes, over time, the color with exposure to light. Proximal to this portion, on the external surface of body member can be imprinted areas of various colors 95, resembling the colors of the material at different stages of light exposure. Resemblance of the color of said material to a certain imprinted color will indicate the end of the useful lifetime of the device. Such color changing materials are diazo resins such as the polymethylene para-diazo diphylamine sulfate. The exterior portion of the material can be protected from changing light due to exposure of ambient light by a coating that is clear in the visible area and blocks light in the photosensitive spectrum. Alternatively it can be covered by a retractable cover that allows viewing only when the color of said material is evaluated.

Figure 6:
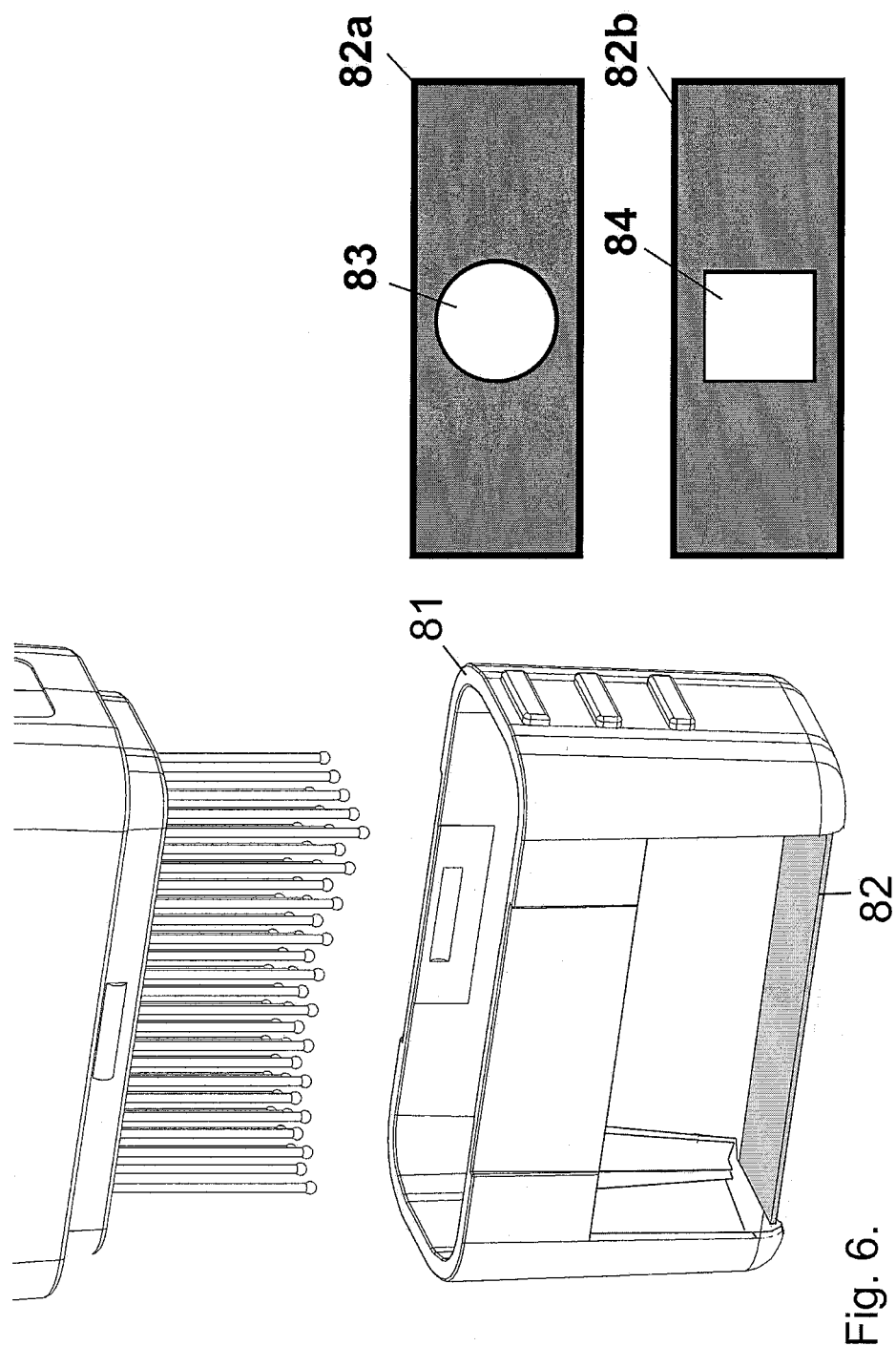
FIG. 6 shows a diffuser cap for the device with elements for producing alternative shapes.
Figure 7:
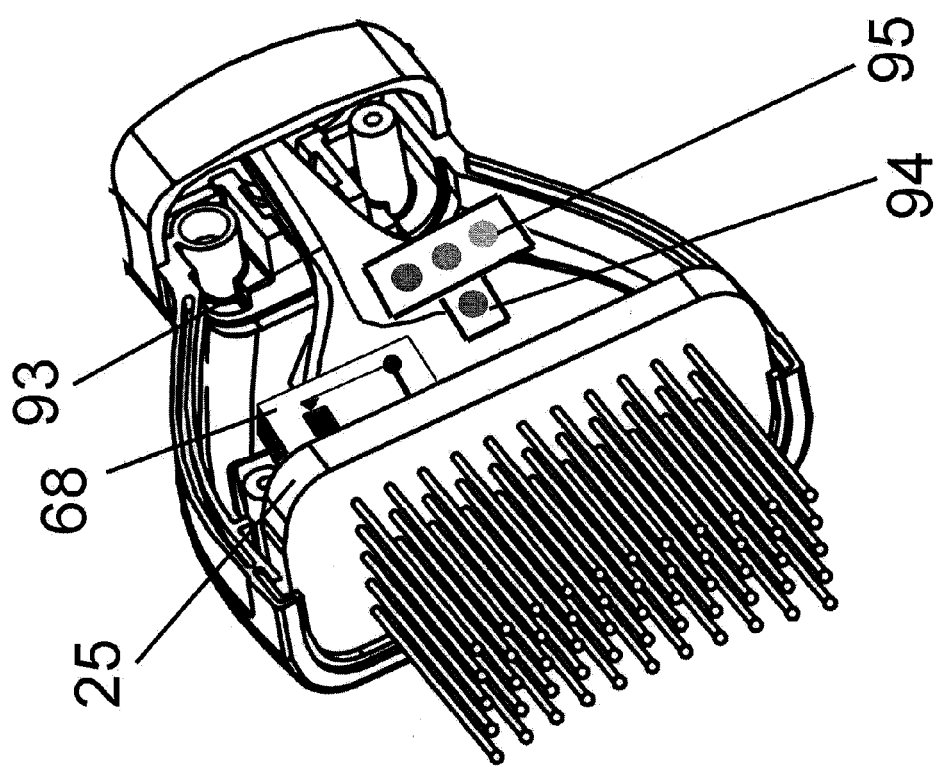
FIG. 7 shows an indicator on brush body that changes color with use.

A different cap 81 (FIG. 6) of similar material can be detachably attached to the Fiberoptic Brush. This cap will have at the bottom a light diffusing plate 82 to diffuse and homogenize the light for treatment of areas that are not covered by hair. The cap is secured on the brush in a manner similar to the rinse cap 46. Different size and shape diffuser plates 82a, 82b can provide various profiles 83, 84 for treatment of specific areas and lesions. The profiles can be selected so that they match the size and shape of the lesions. Alternatively, cap 81 can have no diffusing elements but openings of various shapes and sizes, acting as a distance gage and allowing the light exiting from each fiber to blend and produce uniform field of and deliver consistent intensity, since the intensity changes with distance from the tips of the light transmitting elements since the exiting beam is diverging.

As mentioned above, the therapeutic light will be coupled from the light source to the Fiberoptic Brush 100 via a light guide that can be a fiber bundle 71 or a liquid filled flexible tube. The coupling can consist, on the brush side, of a protrusion 72 that has lips 73 with indentations 74 and extrusion 75 for snapping onto a coupler cap 76 that has appropriate shape to fit the Fiberoptic Brush protrusion with an indent 77 for locking the protrusion of the coupling to the coupling cap. The coupling cup is formed of a molded resinous material, such as plastic, rubber, and the like. A boot 79 made out of flexible molded resinous material, such as plastic, rubber, and the like holds that cap onto the light guide and also acts as a strain relief.

Additionally or alternatively, the light coupling can include a connector 78 that connects to the fiber bundle ferrule 35. This connector provides for the alignment and proper distance between the light guide and the fiberoptic bundle.

The therapeutic device described above can be easily used to treat inflammatory dermatoses affecting body regions covered by hair, such as the scalp. Fibers 24 can be positioned so that the distal tips 27 are pressed gently through such encumbrances to contact the scalp during use. The blunting or rounding of distal tips helps prevent development of the Auspitz sign during normal use.

This device overcomes limitations and provides improvements over existing devices for the treatment of areas of the skin, such as the scalp, and the affected skin areas may be treated without exposing the entire body to 8-MOP and/or to UV light.

Preferred embodiments of the method of treating an inflammatory dermatosis using the aforementioned device are as follows.

For UV-B phototherapeutic treatment, simple application while gently combing through the hair for prescribed times necessary is acceptable, beginning with approximately one minimum erythema dose (MED) during the first treatment. Subsequent treatment times would increase if needed and as tolerated by the skin.

Natural skin oils, water, or light lubricants applied to the scalp may beneficially modify the optics of psoriatic skin, further reduce trauma, and provide good index matching to silica fibers. The delivery of UV radiation into the skin via direct contact with a UV-transmitting optical fiber is more efficient than through air, due to refractive index mismatching between the skin ($n_d$=1.55) and air ($n_d$=1.00). By directly contacting the scalp with the preferred fiber optic core material, fused silica ($n_d$=1.46), specular reflection at the scalp surface is greatly reduced, especially when a lubricant or topical application of psoralen-containing solution is present. The amount of such specular reflection varies mainly with the square of the difference in psoriasis, there is poor formation of the outermost skin layer. Thus, coupling of UV light into the psoriasis skin is much more efficient with direct contact between t Of course, other areas of the skin such as the nails could also be treated as described above.

CLINICAL EXAMPLES

The following describes the clinical use of a phototherapy device and methods of the type described above.

Figure 8:
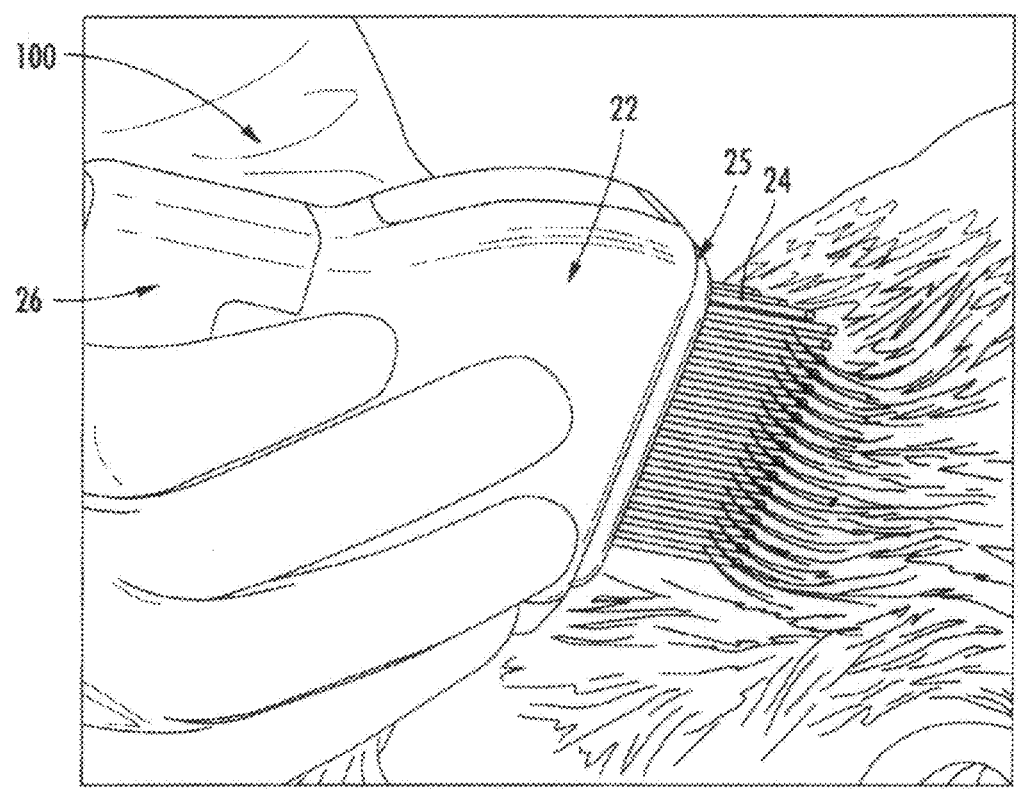
FIG. 8 is a photograph of an exemplary phototherapy device in clinical use.

As shown in FIG. 8, the scalps of patients were treated with a fiberoptic brush phototherapy device 100 of the type described above. The bristles of the brush consisted of optical fibers 24 allowing combing to deliver light to the scalp. Without this delivery system hair would absorb light and prevent it from reaching the scalp. Mineral oil was applied as in the spot treatment. Exposure levels were similar to those noted above for non-scalp areas. The phototherapy device 100 produced 25 mW/cm2 at full output. The output level was varied to allow delivery of the appropriate dose. FIG. 9 shows a table of exemplary dosages for various classifications of skin type, as will be understood by those skilled in the art.

Figure 10:
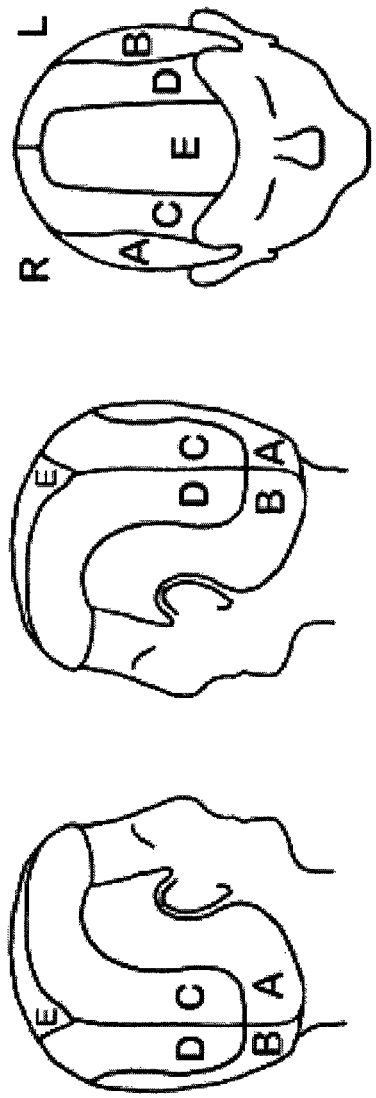
FIG. 10 is an illustration showing the division of a human scalp into treatment areas.

As illustrated in FIG. 10, in patients with a full head of hair, the scalp was divided into five zones A, B, C, D, E. The zones were treated for time intervals that ranged from thirty seconds to four minutes. The treatment time for the entire scalp reached a maximum of fifteen minutes. For patients with skin Type II, as is know in the art, the initial dose was set at 2 MEDs and was increased by 15-20% on each treatment. The hair was parted at that area with the fingers. If the patient complained of burning sensation discomfort, the dose was not increased or the increase was moderated. The same applied on the few occasions the patient skipped a treatment. Patients were treated twice a week for a total of twelve treatments. If spots cleared earlier, treatment was discontinued when there was no visible lesion or hyperpigmentation on the skin. Considering that some patients missed a treatment now and then, the total time was 7-8 weeks. For the scalp preservation treatment was given once per week or every other week.

Patient 1 was a Caucasian male, 35 years old with skin type: III. His medical history included: stable psoriatic plaques on the scalp last 5 years. Previous treatment involved emollients, steroid creams, peanut oil, and tar shampoos. No topical (or systemic) treatments were given for 4 weeks prior to targeted UVB therapy. The patient's treatment occurred two times a week for a total of twelve treatments. The scalp was treated with a fiberoptic brush phototherapy device of the type described above. For the scalp, the initial dose was 180 mJ/cm$^2$ and was increased by 15-20% on each treatment until it reached 950 mJ/cm$^2$. On the scalp, clearance was achieved with 8 treatments. Preservation treatment was continued once a week for 6 weeks. The patient was clear on the last examination, 4 weeks after the last treatment.

Patient 2 was a Caucasian male, 27 years old with skin type II. His medical history included: stable psoriatic plaques on head, arms, legs and body. Previous treatment involved emollients, tar shampoos, occasional steroid creams, and various herbal therapies. No topical or systemic treatments were provided for 4 weeks prior to targeted UVB therapy. The scalp was treated with a fiberoptic brush phototherapy device of the type described above. Patient 2's treatment was similar to patient 1 but cleared faster and treatment was discontinued. The patient cleared after 6 weeks of treatment (ten treatments) and treatment was interrupted once he was clear. Preservation treatment was not given. The patient was clear on the last examination, 8 weeks after treatment.

Patient 3 was a Caucasian male, 52 years old with skin type II. His medical history included: stable psoriatic plaques on the scalp. Previous treatment involved emollients, steroid creams, and tar shampoos. No topical (or systemic) treatments were given for 4 weeks prior to targeted UVB therapy. Treatment was provided two times a week for a total of twelve treatments. The scalp was treated with a fiberoptic brush phototherapy device of the type described above. For the scalp, the initial dose was 150 mJ/cm$^2$ (about 2 MEDs) and was increased by 15-20% on each treatment until it reached 750 mJ/cm$^2$. On the scalp, clearance was achieved with 8 treatments. Preservation treatment was continued once a week. The patient was delighted with the results.

In the above examples Psoriatic lesions began to resolve after 3-4 treatments and the majority of the lesions cleared within 8-10 treatments. Tanning was observed in the treated areas. The patients were evaluated monthly following phototherapy.

Use of a fiberoptic brush type phototherapy device of the type described above resulted in successful treatment of scalp psoriasis. It was easy for the operator to perform and well tolerated by the patient. Each session was less than 15 minutes.

One or more or any part thereof of the control, sensing, or other techniques described above can be implemented in computer hardware or software, or a combination of both. The methods can be implemented in computer programs using standard programming techniques following the method and figures described herein. Program code is applied to input data to perform the functions described herein and generate output information. The output information is applied to one or more output devices such as a display monitor. Each program may be implemented in a high level procedural or object oriented programming language to communicate with a computer system. However, the programs can be implemented in assembly or machine language, if desired. In any case, the language can be a compiled or interpreted language. Moreover, the program can run on dedicated integrated circuits preprogrammed for that purpose.

Each such computer program is preferably stored on a storage medium or device (e.g., ROM or magnetic diskette) readable by a general or special purpose programmable computer, for configuring and operating the computer when the storage media or device is read by the computer to perform the procedures described herein. The computer program can also reside in cache or main memory during program execution. The technique can also be implemented as a computer-readable storage medium, configured with a computer program, where the storage medium so configured causes a computer to operate in a specific and predefined manner to perform the functions described herein.

As used herein the terms "light," "optics," "optical," etc are to be understood to include electromagnetic radiation both within and outside of the visible spectrum, including, for example, ultraviolet radiation.

The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein.

What is claimed:

1. An apparatus adapted for use as a phototherapy device, comprising:
    a body member;
    a plurality of elongated light transmitting elements, each of said elements extending between a proximal end enclosed within the body member, and a distal end located outside of and distal to the body member and having only bends of less than 90° between the proximal ends and the distal ends; wherein the tips of the proximal ends of the light transmitting elements are located in close proximity to each other and the tips of the distal ends are spaced apart in an array; and wherein each of said proximal ends extends along an input axis, and each of said distal ends extends along an output axis, and wherein the input axes are mutually parallel, the output axes are mutually parallel, and the input axes are parallel to the output axes; and
    an optical connector configured to detachably receive an end of a lightguide and to couple light delivered by the lightguide from a source into the light transmitting elements at the proximal ends;
    wherein the light coupled into each of the light transmitting elements is transmitted along the element and emitted from the distal end;
    wherein the light transmitting elements each comprise an optical fiber;
    wherein the proximal ends of the light transmitting elements comprise a fiber bundle, said bundle having an entrance face comprised of the tips of the proximal ends;
    wherein the fibers of the fiber bundle are fused together in proximity to the entrance face, such that the light emitted from the distal ends has substantially uniform fluence.

2. The apparatus of claim 1 wherein the light transmitting elements are detachably affixed to the body member.

3. The apparatus of claim 1, comprising an optically transparent window positioned in proximity to the entrance face and transverse to the input axis.

4. The apparatus of claim 1, wherein each of the fibers in the fiber bundle comprise an inner core surrounded by a cladding, and wherein the cladding is stripped away from a portion of the fiber in proximity to the entrance face.

5. The apparatus of claim 1, comprising a ring adapted to secure the fibers in the fiber bundle in close proximity to each other.

6. The apparatus of claim 1, wherein the optical connector is adapted to hold an end of the lightguide in fixed spatial alignment with the face of the fiber bundle.

7. The apparatus of claim 1, wherein the distal ends of the light transmitting elements are arranged in an array.

8. The apparatus of claim 7, wherein the array is a two dimensional array.

9. The apparatus of claim 7, wherein the tips of the distal ends of the light transmitting elements are located at positions in space having a locus characterized by a curved surface or arc.

10. The apparatus of claim 9, wherein the curved surface or arc comprises one of the group of: a circular arc, a parabolic arc, and ellipsoidal arc, a cylindrical segment, a spherical segment, a toroidal segment.

11. The apparatus of claim 10, where the curved surface or arc has an associated radius or radii or curvature within the range of about 2 inches to about 6 inches.

12. The apparatus of claim 9 wherein the locus is adapted to substantially conform to the shape of a human scalp.

13. The apparatus of claim 7, wherein the array is arranged to provide substantially uniform fluence of light emitted from the distal ends of the light transmission elements at an area of a treatment surface.

14. The apparatus of claim 1, wherein the distal end of one or more of the light transmitting elements comprises a bulbous tip comprised of a light emitting spherical segment.

15. The apparatus of claim 14, wherein the spherical segment has a radius of curvature within the range of about 0.25 mm to about 3.0 mm.

16. The apparatus of claim 1, wherein the distal end of one or more of the light transmitting elements comprises a rounded tip.

17. The apparatus of claim 16, wherein the rounded tip has a radius of curvature within the range of about 0.25 mm to about 3.0 mm.

18. The apparatus of claim 1, wherein the fiber comprises an inner core surrounded by an outer cladding, said inner core having a radius within the range of about 0.1 mm to about 3 mm.

19. The apparatus of claim 1, wherein the elongated light transmitting elements are autoclavable.

20. The apparatus of claim 1, further comprising a cap adapted for removable connection to the body member, said cap adapted to, when connected to the body member, enclose the distal ends of the light transmitting elements.

21. The apparatus of claim 20, wherein the cap comprises an optical diffuser element disposed between the tips of the distal ends of the light transmitting elements and a treatment area.

22. The apparatus of claim 1, further comprising a control unit enclosed in the body member wherein the control unit is in communication with the light source, and the control unit adapted to selectively adjust the duration or intensity of light provided from the source through a lightguide.

23. The apparatus of claim 22, further comprising a sensor adapted to determine information indicative of the intensity of light emitted from the distal ends of the light transmitting elements.

24. The apparatus of claim 23, wherein the control unit is configured to, based on the information indicative of the intensity of light from the distal ends of the light transmitting elements, adjust the duration or intensity of light provided from the source to maintain constant output intensity.

25. The apparatus of claim 22, further comprising a dosimetry sensor adapted to, during operation, provide to the control unit information indicative of a dose of treatment light directed from the light transmitting elements to a treatment surface.

26. The apparatus of claim 25, wherein the control unit is configured to selectively adjust the duration and intensity of light coupled into the light transmitting elements based on said information indicative of the dose of treatment light.

27. The apparatus of claim 1, further comprising the lightguide and the source.

28. The apparatus of claim 27, wherein the source has a spectral range within the range of 280 nm to 320 nm.

29. The apparatus of claim 28, wherein the source has a spectral range within the range of 308 nm to 320 nm.

30. The apparatus of claim 27, wherein the source has a spectral range within the range of 320 nm to 380 nm.

31. The apparatus of claim 27, wherein the source comprises at least one of the group of: a lamp, a laser, an excimer laser, a diode laser, a light emitting diode, an excimer gas discharge lamp.

32. The apparatus of claim 22, further comprising a sensor adapted to sense the proximity or contact of the distal end of one or more of the elongated light transmitting elements to a treatment surface, said sensor being in communication with the control unit.

33. The apparatus of claim 22, further comprising an auditory signal transducer in communication with the control unit.

34. The apparatus of claim 1, further comprising a substance adapted to change color over time with exposure of light, and wherein one or more of the light transmitting elements has a distal end opposite the substance.

35. The apparatus of claim 1, wherein one or more of the elongated light transmitting elements comprises a hollow tube, the interior surface of said tube having a reflective coating.

36. A method of treating an area of skin affected by inflammatory skin disease comprising:
providing an effective dose of treatment light to the affected area with an apparatus adapted for use as a phototherapy device, said device comprising:
a body member;
a plurality of elongated light transmitting elements, each of said elements extending between a proximal end enclosed within the body member and a distal end located outside of and distal to the body member and having only bends of less than 90° between the proximal ends and the distal ends; wherein the tips of the proximal ends of the light transmitting elements are located in close proximity to each other and the tips of the distal ends are spaced apart in an array; and wherein each of said proximal ends extends along an input axis and each of said distal ends extends along an output axis, and wherein the input axes are mutually parallel and the output axes are mutually parallel, and wherein the input axis is parallel to the output axis; and
an optical connector configured to detachably receive an end of a lightguide and to couple light delivered by the lightguide from a source into the light transmitting elements at the proximal ends;
wherein the light coupled into each of the light transmitting elements is transmitted along the element and emitted from the distal end;
wherein the light transmitting elements each comprise an optical fiber;
wherein the proximal ends of the light transmitting elements comprise a fiber bundle, said bundle having an entrance face comprised of the tips of the proximal ends;
wherein the fibers of the fiber bundle are fused together in proximity to the entrance face; and
wherein each of the fibers in the fiber bundle comprise an inner core surrounded by a cladding, and wherein the cladding is stripped away from a portion of the fiber in proximity to the entrance face such that the light emitted from the distal tips has substantially uniform fluence.

37. The method of claim 36, wherein the treatment light comprises ultraviolet light.

38. The method of claim 37, wherein providing treatment light comprises bringing the distal ends of the light transmitting elements into proximity or contact with the affected area.

39. The method of claim 38, wherein the providing treatment light comprises, while maintaining distal ends of the light transmitting elements into proximity or contact with the affected area, moving the distal ends across the affected area to provide at least one minimal erythema dose of treatment light to substantially the entire the affected area.

40. The method of claim 39, wherein at least a portion of the affected area is a hair bearing region, and moving the distal ends across the affected area comprises combing the distal ends through the hair.

* * * * *